(12) United States Patent
McElroy et al.

(10) Patent No.: US 8,317,764 B2
(45) Date of Patent: Nov. 27, 2012

(54) DESIGNING THE SHAPE OF ABSORBENT ARTICLES WORN CLOSE TO THE BODY

(75) Inventors: Elizabeth Rachelle McElroy, Cincinnati, OH (US); Beth Goldman Mason, Anderson Township, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 892 days.

(21) Appl. No.: 11/708,246

(22) Filed: Feb. 20, 2007

(65) Prior Publication Data

US 2008/0015529 A1 Jan. 17, 2008

Related U.S. Application Data

(63) Continuation-in-part of application No. 11/487,069, filed on Jul. 14, 2006, now abandoned.

(51) Int. Cl.
*A61F 13/15* (2006.01)
*A61F 13/20* (2006.01)
(52) U.S. Cl. .................................. 604/385.01; 604/358
(58) Field of Classification Search ............. 604/385.01, 604/358
See application file for complete search history.

(56) References Cited

U.S. PATENT DOCUMENTS 6,810,300 B1 * 10/2004 Woltman et al. ............. 700/132

FOREIGN PATENT DOCUMENTS

WO 2005/088582 A2 * 9/2005

OTHER PUBLICATIONS

Woodward, Carol, Clothing Care & Sewing Techniques for Visually Impaired or Totally Blind Students, Mar. 1998, pp. 1-12.*
Jones (2000), Fashion Design, Watson-Guptill Publications, pp. 118-125.
Gioello, D.A. and Berke, Beverly (1979) Fashion Production Terms, Fairchild Books & Visuals, pp. 37-50.
Armstrong (1995), Pattern Making for Fashion Design, 2nd Edition, Harper Collins College Publishers, pp. 8-15.

* cited by examiner

*Primary Examiner* — Michele M Kidwell
(74) *Attorney, Agent, or Firm* — Megan C. Hymore; James Oehlenschlager

(57) ABSTRACT

A method for designing an absorbent article to be worn close to the body is disclosed. For one embodiment of the method, the steps are attaching middy tape in the shape of an edge of a first element of an absorbent article onto a body form to create an outline of the first element of the absorbent article, attaching conformable sheet material to the body form about the outline of the first element of the absorbent article, marking the shape of the outline of the first element of the absorbent article on the conformable sheet material to create a pattern, removing the conformable sheet material from the body form, constructing a first element of the absorbent article corresponding to the pattern.

20 Claims, 4 Drawing Sheets

DESIGNING THE SHAPE OF ABSORBENT ARTICLES WORN CLOSE TO THE BODY

CROSS REFERENCE TO RELATED APPLICATION

This application is a continuation-in-part of U.S. Ser. No. 11/487,069, filed on Jul. 14, 2006 now abandoned.

FIELD OF THE INVENTION

The invention relates to a method for designing the shape of absorbent articles worn close to the body.

BACKGROUND OF THE INVENTION

The human body has curves of varying curvature and various folds. To perform optimally, absorbent articles worn close to the body need to conform to the shapes of the body's curves and folds. Absorbent articles are typically comprised of multiple layers of materials that are thin relative to their planar dimensions. Thus, one problem facing designers of absorbent articles to be worn close to the body is how to translate what are essentially two-dimensional pieces of material into a shape that conforms to a three-dimensional shape.

Absorbent articles worn close to the body perform by capturing excretions of fluids from the body. For absorbent articles including sanitary napkins, panti-liners, incontinence articles, diapers, and breast pads, the portion of the body from which the excretions emanate are well defined. Designers desire that these types of absorbent articles remain in close contact with the wearer's body so that the absorbent article captures the fluid without permitting any fluid to bypass the absorbent article. Fluid that bypasses an absorbent article worn close to the body can end up soiling the wearer's outer clothing, resulting in a potentially embarrassing situation.

Wearers of absorbent articles are involved in a wide variety of activities in which the shape of the body is continually changing. For instance, an infant diaper wearer may spend part of her day lying down and sitting and another part of her day crawling. Similarly, adults are involved in a wide range of activities ranging from lying and sitting to running and playing sports. The absorbent article that an adult wears needs to fit her body throughout a range of different activities.

One approach to designing the shape of absorbent articles is to create body forms, such as mannequins, having a variety of body geometries and body positions and placing prototypes of absorbent articles in contact with the body form to evaluate how well they fit the body form. If the absorbent article does not fit the body form well, the designer alters the shape of the absorbent article. The designer may alter the shape of the article by adding or removing material and may alter the thickness or thinness of the absorbent article. This approach to design can be cumbersome and may not yield the optimum conformance of the absorbent article. One possible reason that this approach may not lead to satisfactory results is because the design problem is viewed as "how can a three dimensional shape be designed to conform to a body?" An alternative view is to frame the design problem as "what shapes of two dimensional materials can be used to form a three-dimensional absorbent article that conforms to a body?" Another approach to designing the shape of absorbent articles is to use three-dimensional images of bodies collected using a device such as a magnetic resonance imaging apparatus. Magnetic resonance imaging can provide exceptionally detailed information on the shape of the surface of the human body. To use this method, a designer must have access to an expensive imaging device, computational tools enabling analysis and manipulation of collected images, and subjects who are able and willing to submit to being imaged.

There is a continuing unaddressed need for methods for designing absorbent articles that conform to the shape of the body. There is a continuing unaddressed need for methods for designing absorbent articles that conform to the shape of the body that are inexpensive to use and relatively easy to perform.

SUMMARY OF THE INVENTION

A method for designing an absorbent article to be worn close to the body is disclosed. In a first embodiment, the steps of the method are attaching middy tape in the shape of an edge of a first element of an absorbent article onto a body form to create an outline of the first element of the absorbent article, attaching conformable sheet material to the body form about the outline of the first element of the absorbent article, marking the shape of the outline of the first element of the absorbent article on the conformable sheet material to create a pattern, removing the conformable sheet material from the body form, and constructing a first element of the absorbent article corresponding to the pattern. An additional step of the first embodiment of the method can be truing the pattern. The conformable sheet material can be the same material as that used to construct the first element of the absorbent article.

In a second embodiment of the method, the steps are attaching a first element of an absorbent article to a body form, attaching middy tape in the shape of an edge of a second element of an absorbent article to the body form to create an outline of the second element of the absorbent article, attaching conformable sheet material to the body form about the outline of the second element of the absorbent article, marking the shape of the outline of the second element of an absorbent article on the conformable sheet material to create a pattern, removing the conformable sheet material from the body form, constructing a second element of the absorbent article corresponding to the pattern. An additional step of the second embodiment of the method can be marking reference points on the first element and second element. In the second embodiment of the method, the conformable sheet material can be the same material as that used to construct the second element of the absorbent article.

In both embodiments, the conformable sheet material can be selected from the group consisting of a topsheet, a secondary topsheet, an absorbent core, and a backsheet. In both embodiments, the first element can be selected from the group consisting of a topsheet, a secondary topsheet, an absorbent core, and a backsheet. In both embodiments, the absorbent article can be selected from the group consisting of a panti-liner, a sanitary napkin, an incontinence device, a diaper, a wound dressing, and a breast pad. In both embodiments, the body form can be of a body in a position selected from the group consisting of lying, standing, sitting, walking, running, sitting cross-legged, and squatting. In both embodiments, the body form can be selected from the group consisting of an adult female, an adult male, an adolescent male, an adolescent female, an infant female, an infant male, a female toddler, and a male toddler.

DETAILED DESCRIPTION OF THE INVENTION

Figure 1:
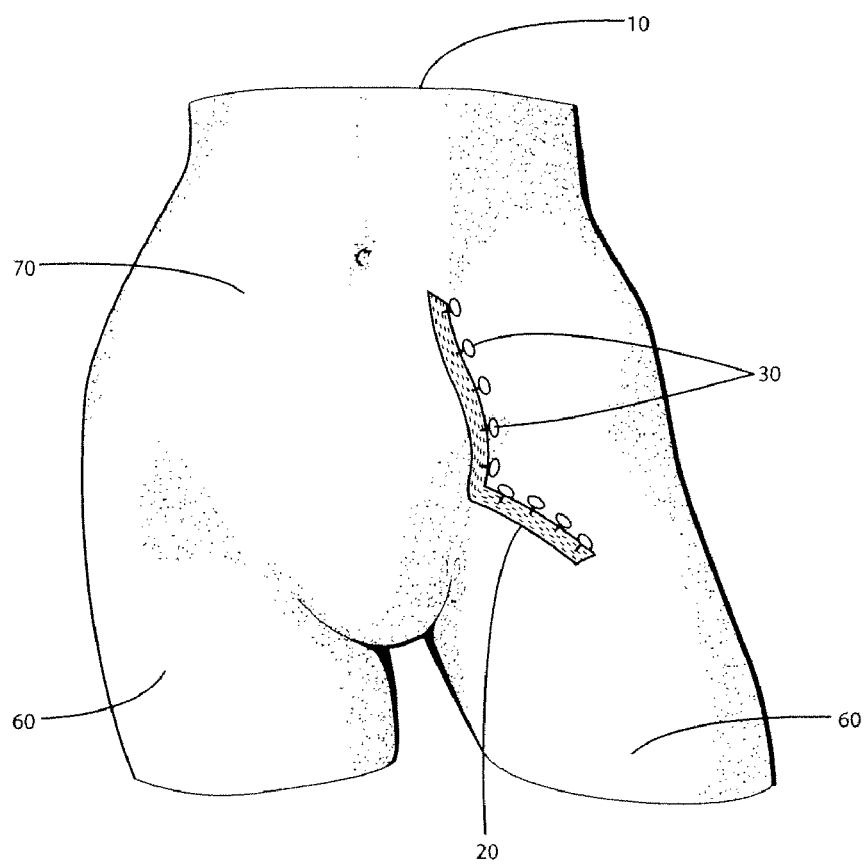
FIG. 1 is an illustration of middy tape attached to a torso.

A body form 10 upon which the method disclosed herein can be used is illustrated in FIG. 1. The body form 10 can include representation of a pair of legs 60 and lower abdomen 70. The body form 10 can correspond to an actual body engaged in some activity including, but not limited to, lying, standing, sitting, walking, running, sitting cross-legged, squatting, or any other body position. The body form 10 can correspond to an adult female, an adult male, an adolescent female, an adolescent male, an infant female, an infant male, a female toddler, and a male toddler. The body form should correspond to a typical body form of a person who might wear the absorbent article being designed.

The body form 10 can be a living person. The person can maintain a pose of a person engaged in some activity including, but not limited to, lying, standing, sitting, walking, running, sitting cross-legged, squatting, or any other body position.

The body form 10 can correspond to the shape of an ideal body or the body of a person who is underweight or overweight. The body form 10 can correspond to the shape of a mature body or an adolescent body. The body form can be comprised of a material into which pins may be penetrated relatively easily or to which items can be adhered to easily. For instance, the body form 10 can be formed from rigid STYROFOAM or may be formed from pliable conformable sheet material that is stuffed with a soft wadding material. The body form 10 can also be plastic or rubber.

Middy tape 20 is attached in the shape of an edge of a first element of an absorbent article onto the body form 10 to create an outline of a first element of an absorbent article. Middy tape 20 is a material sold in sewing supply stores and is referred to by those skilled in the art as "Middy Tape." A flat braided rope that is about 3 to about 7.5 mm wide is also suitable. Middy tape 20 has a dark color, such as black, that can be easily seen through semi-transparent materials. A suitable middy tape 20 is Middy Braid 117-531, colored black, available from JKM Ribbons & Trims, West Berlin, N.J.

The first element can be any component or portion of a component of an absorbent article including, but not limited to, a topsheet, a secondary topsheet, an absorbent core, or a backsheet. The absorbent article can be a panti-liner, a sanitary napkin, an incontinence device, a diaper, a wound dressing, a breast pad, or any other type of absorbent article that is designed to be worn close to the body.

Figure 2:
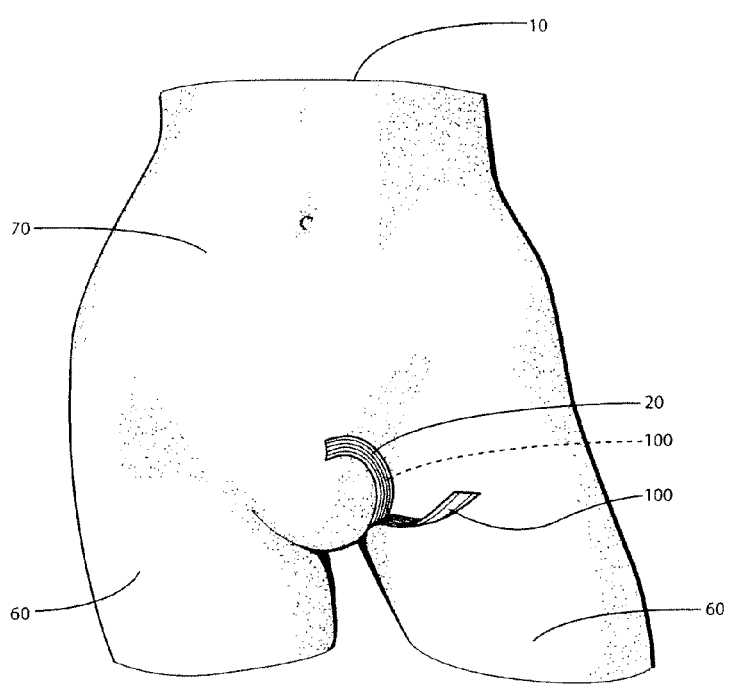
FIG. 2 is an illustration of middy tape comprising a pressure sensitive adhesive, the middy tape being partially attached to a torso.

The middy tape 20 can be attached to the body form 10 using pins 30. Pins 30 can be pins commonly used by those who sew. Alternatively, the middy tape 20 can be attached to the body form using an adhesive or an adhesive tape. The middy tape 20 should be attached to the body form 10 in enough locations such that the shape of the outline of the first element is rendered in sufficient detail to capture the curvature of the body where the absorbent article will be worn. If sewing pins 30 are used, the pins can be spaced apart by as much as about 1.5 cm and as closely spaced as about 1 mm. Middy tape 20 can further comprise pressure sensitive adhesive 100 on the middy tape 20 so that the middy tape 20 can be attached to the body form 10 without using pins 30. If the body form 10 is a living person, the peel strength of a pressure sensitive adhesive 100, if used, should be low enough to prevent pain or injury to the person from peeling the middy tape 20 from the person's body. FIG. 2 illustrates middy tape comprising a pressure sensitive adhesive on one surface attached to a torso.

If the absorbent article has a symmetrical shape and will be worn on a portion of the body that is symmetrical, middy tape 20 needs to be attached only on one side of the line of symmetry.

For a sanitary napkin or panti-liner to be worn in wearer's crotch region, the designer can place the middy tape 20 along an edge of the pudendal region. Many sanitary napkins and panti-liners cover the vaginal area and partially cover the pubic area. A woman's crotch tends to be curved and her body tends to have a curved transition between her crotch and pubic areas. The width of the absorbent article may vary from being narrow in the crotch area to being broader in the pubic area. Thus, as the middy tape 20 is attached to the body form 10, the middy tape 20 outlines a three-dimensional shape that corresponds to the shape of the body form 10.

Figure 3:
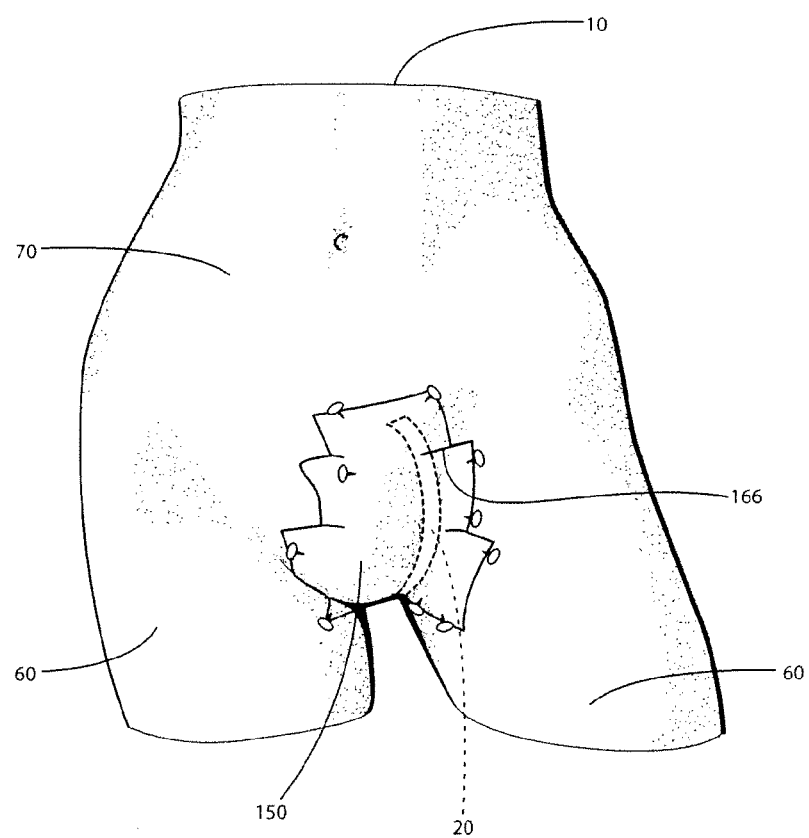
FIG. 3 is an illustration of the conformable sheet material attached to a torso.

Once the shape of an edge of a first element of an absorbent article is attached to the body form 10 to create an outline of the first element of an absorbent article, conformable sheet material 150 is attached to the body form 10 about the outline of the first element of the absorbent article. As shown in FIG. 3, if the absorbent article is to be worn in an area of the body that is symmetric, conformable sheet material 150 needs to be attached to only a portion of the body form on one side of the line of symmetry. The conformable sheet material 150 can be attached to the body form 10 using pins 30. The pins 30 used for attaching the conformable sheet material 150 can be the same kind as those used to attach the middy tape 20 to the body form 10.

The conformable sheet material 150 attached to the body form 10 should be transparent enough such that the middy tape 20, which outlines the shape of the first element, can be seen through the conformable sheet material. The conformable sheet material 150 can be lightweight muslin, the weight of which is chosen to correspond with the element of the absorbent article being designed. If the first component of the absorbent article will be comprised of a material that is transparent enough such that middy tape 20 can be seen through the material, the conformable sheet material 150 can be the same material that will be used to construct the absorbent article. The conformable sheet material can be a topsheet, a secondary topsheet, an absorbent core, or a backsheet of an absorbent article such as a sanitary napkin, panti-liner, incontinence product, diaper, wound dressing, or breast pad. High loft materials such as absorbent cores can be used as the conformable sheet material 150.

To fit the conformable sheet material 150 to the body form 10, portions of the conformable sheet material 150 may need to be pleated or folded so that the conformable sheet material 150 conforms to the three-dimensional shape of the body form 10. FIG. 3 illustrates a number of pleats 166.

Figure 4:
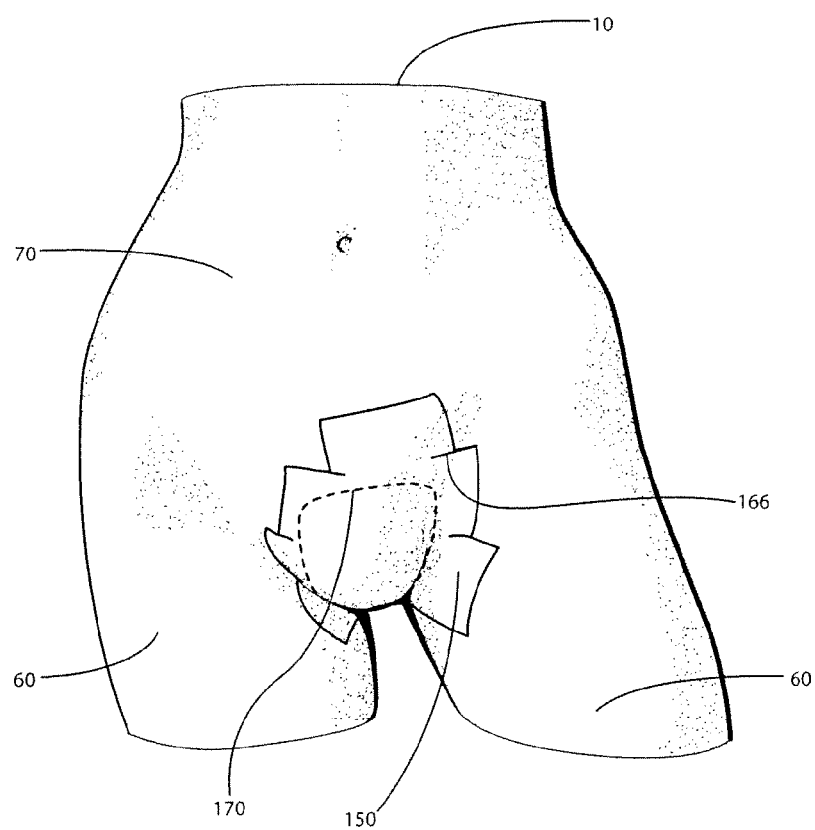
FIG. 4 is an illustration of the conformable sheet material attached to a torso and the pattern.

Once the conformable sheet material 150 is attached to the body form 10 about the outline of the first element of an absorbent article, the shape of the outline of the first element of an absorbent article is marked on the conformable sheet material to create a pattern 170, shown in FIG. 4. The conformable sheet material 150 can be marked with an ordinary ink marker. The conformable sheet material 150 can be marked using small dots spaced apart by as much as about 1.5 cm and as closely spaced as about 1 mm.

After the pattern 170 is completed, the conformable sheet material 150 is removed from the body form 10.

Once the conformable sheet material 150 is removed from the body form 10, the pattern 170 can be trued if desired. The pattern 170 is comprised of a number of small dots marked on the conformable sheet material 150. If the dots are connected by straight lines, the pattern 170 is a polygon. The closer the dots are together to one another, the more closely the polygon will conform to the shape of the body form 10. Ideally, the dots of the pattern 170 should be connected with smooth curves because the body is comprised of smooth curves, not straight lines. Truing is a step by which the portions of the pattern 170 between adjacent dots of the pattern 170 are connected by smooth curves. Truing can be performed "by eye" or a French curve, flexible curve, or hip curve can be used to help the designer connect the marked dots with smooth curved lines. The decision of whether or not truing will improve the design can be made by a subjective judgment in which the designer looks at the shape and determines if curvature of the body form 10 is sufficiently captured.

Based on the pattern 170, a first element of the absorbent article corresponding to the pattern 170 is constructed. The pattern 170 can be cut from the conformable sheet material 150 to make a pattern 170 used to guide construction of the first element. The first element can be constructed by cutting material that will actually be used in the absorbent article to have the shape of the pattern 170. If only a side of a symmetric absorbent article is marked, the other side of the absorbent article can be marked based on symmetry.

The design method can be used to design absorbent articles comprised of more than one layer. To employ the design method, the first element of an absorbent article is attached to the body form 10. The first element is a component or portion of a component of an absorbent article that is closer to the body than a second element when the absorbent article is worn. The first element can be components or portions of components of the absorbent article that are closer to the body than the second element. For instance, a sanitary napkin typically comprises a topsheet that is in contact with the body, a backsheet that is adhered to the wearer's panty, and an absorbent core disposed between the topsheet and backsheet. The first element can be the topsheet and the second element can be an absorbent core. The first element can be the topsheet and the second element can be a secondary topsheet. The first element can be the combination of the topsheet and absorbent core and the second element can be the backsheet. The first element can be the combination of the topsheet, absorbent core, and backsheet and the second element can be another component of the absorbent article adjacent to the backsheet. In this manner, the design method can be used to design elements of the absorbent article that are separated from the body by one or more other elements of the absorbent article.

Once the first element is attached to the body form 10, the steps of the design process are the same as those discussed above. The only difference is that the steps are performed on a body form 10 to which a first element is already attached and the method leads towards constructing a second element of the absorbent article.

Once the first element is attached to the body form 10, the middy tape 20 is attached atop or around the first element in the shape of an edge of a second element of the absorbent article to the body form 10 to create an outline of the second element of the absorbent article. The outline of the second element of the absorbent article is placed over the body form 10 and the first element. The outline of the second element need not have the same dimensions as the first element. Portions of the outline of the second element can lie within the boundary of the first element, portions of the outline of the second element can lie beyond the boundary of the first element, and portions of the outline of the second element can coincide with the boundary of the first element.

After the outline of the second element of the absorbent article is formed, conformable sheet material 150 is attached to the body form about the outline of the second element of the absorbent article. The shape of the outline of the second element of the absorbent article is marked on the conformable sheet material 150 to create a pattern 170. The conformable sheet material 150 is then removed from the body form. The pattern 170 is then used to construct a second element of the absorbent article that corresponds with pattern 170. Reference points can be marked on the first element and second element to help the designer coordinate the location and orientation of the second element relative to the first element. Marking can be performed with an ink pen, chalk, pencil, pins, by notching the materials with scissor cuts, or any other suitable method for marking materials such that the spatial relationship between layers of materials can be referenced later.

The pattern 170 of the outline of the second element can be trued using the same method as described above with respect to truing the pattern 170 of the first element. The conformable sheet material upon which the pattern 170 of the outline of the second element is created can be the same material that will be used to construct the second element of the absorbent article. The pattern 170 of the outline of the second element can be used to guide construction the second element.

The method can be continued for as many elements as desired by successively layering on additional elements and repeating the steps above. Each pattern created using the method can be used to guide construction of each individual layer.

The absorbent article can be selected from the group consisting of a panti-liner, a sanitary napkin, an incontinence device, a diaper, a wound dressing, and a breast pad.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference. The citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for designing an absorbent article to be worn close to the body comprising the steps of:
    attaching middy tape in the shape of an edge of a first element of an absorbent article to a material body form to create an outline of said first element of said absorbent article;
    attaching conformable sheet material to said material body form about said outline of said first element of said absorbent article;

marking the shape of said outline of said first element of said absorbent article on said conformable sheet material to create a pattern;

removing said conformable sheet material from said material body form; and constructing a first element of said absorbent article corresponding to said pattern.

2. The method according to claim 1 comprising the additional step of truing said pattern.

3. The method according to claim 1 wherein said conformable sheet material is the same material as that used to construct said first element of said absorbent article.

4. The method according to claim 1 wherein said conformable sheet material is selected from the group consisting of a topsheet, a secondary topsheet, an absorbent core, and a backsheet.

5. The method according to claim 1 wherein said first element is selected from the group consisting of a topsheet, a secondary topsheet, an absorbent core, and a backsheet.

6. The method according to claim 1 wherein said absorbent article is selected from the group consisting of a panti-liner, a sanitary napkin, an incontinence device, a diaper, a wound dressing, and a breast pad.

7. The method according to claim 1 wherein said material body form is of a body in a position selected from the group consisting of lying, standing, sitting, walking, running, sitting cross-legged, and squatting.

8. The method according to claim 1 wherein said material body form is of a body selected from the group consisting of an adult female, an adult male, an adolescent male, an adolescent female, an infant female, an infant male, a female toddler, and a male toddler.

9. The method according to claim 1, wherein said middy tape further comprises pressure sensitive adhesive.

10. A method for designing an absorbent article to be worn close to the body comprising the steps of:

attaching a first element of an absorbent article to a material body form;

attaching middy tape in the shape of an edge of a second element of an absorbent article to said material body form to create an outline of said second element of said absorbent article;

attaching conformable sheet material to said material body form about said outline of said second element of said absorbent article;

marking the shape of said outline of said second element of an absorbent article on said conformable sheet material to create a pattern;

removing said conformable sheet material from said material body form; and constructing a second element of said absorbent article corresponding to said pattern.

11. The method according to claim 10 comprising the additional step of marking reference points on the first element and second element.

12. The method according to claim 10 comprising the additional step of truing said pattern.

13. The method according to claim 10 wherein said conformable sheet material is the same material as that used to construct said second element of said absorbent article.

14. The method according to claim 10 wherein said conformable sheet material is selected from the group consisting of a topsheet, a secondary topsheet, an absorbent core, and a backsheet.

15. The method according to claim 10 wherein said first element is selected from the group consisting of a topsheet, a secondary topsheet, an absorbent core, a backsheet, and combinations thereof 16. The method according to claim 10 wherein said second element is selected from the group consisting of a secondary topsheet, an absorbent core, and a backsheet.

17. The method according to claim 10 wherein said absorbent article is selected from the group consisting of a panti-liner, a sanitary napkin, an incontinence device, a diaper, a wound dressing, and a breast pad.

18. The method according to claim 10 wherein said material body form is of a body in a position selected from the group consisting of lying, standing, sitting, walking, running, sitting cross-legged, and squatting.

19. The method according to claim 10 wherein said material body form is of a body selected from the group consisting of an adult female, an adult male, an adolescent male, an adolescent female, an infant female, an infant male, a female toddler, and a male toddler.

20. The method of claim 1, wherein the material body form comprises at least one of STYROFOAM, sheet material stuffed with a soft wadding material, plastic, or rubber.

\* \* \* \* \*